(12) United States Patent
Shelton et al.

(10) Patent No.: US 10,004,521 B2
(45) Date of Patent: Jun. 26, 2018

(54) FEEDBACK DEPENDENT LITHOTRIPSY ENERGY DELIVERY

(71) Applicant: Gyrus ACMI, Inc., Southborough, MA (US)

(72) Inventors: Kurt Shelton, Bedford, MA (US); Lawrence J. St. George, Sudbury, MA (US); Artemie G. Gavala, Sutton, MA (US)

(73) Assignee: Gyrus ACMI, Inc., Southborough, MA (US)

(*) Notice: Subject to any disclaimer, the term of this patent is extended or adjusted under 35 U.S.C. 154(b) by 579 days.

(21) Appl. No.: 14/486,483

(22) Filed: Sep. 15, 2014

(65) Prior Publication Data

US 2015/0133950 A1     May 14, 2015

Related U.S. Application Data

(60) Provisional application No. 61/904,214, filed on Nov. 14, 2013.

(51) Int. Cl.
    *A61B 17/22*      (2006.01)
    *A61B 17/00*      (2006.01)
    *A61B 90/00*      (2016.01)

(52) U.S. Cl.
    CPC .... *A61B 17/2202* (2013.01); *A61B 17/22012* (2013.01); *A61B 90/06* (2016.02);
    (Continued)

(58) Field of Classification Search
    CPC .......... A61B 17/2202; A61B 17/22012; A61B 2090/064; A61B 2090/067; A61B 90/06;
    (Continued)

(56) References Cited

U.S. PATENT DOCUMENTS 4,708,127 A    11/1987   Abdelghani
4,979,952 A    12/1990   Kubota et al.
(Continued)

FOREIGN PATENT DOCUMENTS

EP          1495727 A2    1/2005
JP          62144646 A    6/1987
(Continued)

*Primary Examiner* — Julian W Woo
(74) *Attorney, Agent, or Firm* — Vivacqua Law, PLLC; Gerald P. Kazanjian

(57) ABSTRACT

A lithotripter is provided that includes a lithotripsy apparatus for treatment of a urinary tract stone by fragmentation. The lithotripsy apparatus includes a lithotripsy wave guide shaft configured to transmit an energy form to at least one urinary tract stone. The lithotripter includes a sensing device configured to provide signal data for determining optimal application of energy during treatment with the lithotripsy apparatus. The lithotripter includes a processor configured to collect the signal data and provide feedback to a user. The processor has a control logic configured to determine at least one of: a) if the lithotripsy wave guide shaft is in contact with a tissue; b) if the lithotripsy wave guide shaft is in contact with a stone; c) type of stone; d) if a user is applying force in excess of a predetermined threshold; and e) physical characteristics of a stone. A method is also provided.

16 Claims, 6 Drawing Sheets

(52) U.S. Cl.
CPC ............ *A61B 2017/0011* (2013.01); *A61B 2017/00022* (2013.01); *A61B 2017/00026* (2013.01); *A61B 2017/00039* (2013.01); *A61B 2017/00075* (2013.01); *A61B 2017/00106* (2013.01); *A61B 2017/00119* (2013.01); *A61B 2017/00128* (2013.01); *A61B 2017/00199* (2013.01); *A61B 2017/00402* (2013.01); *A61B 2017/22014* (2013.01); *A61B 2017/22024* (2013.01); *A61B 2090/064* (2016.02); *A61B 2090/065* (2016.02); *A61B 2090/067* (2016.02); *A61B 2217/005* (2013.01)

(58) Field of Classification Search
CPC .... A61B 2090/065; A61B 2017/00199; A61B 2217/005; A61B 2017/00022; A61B 2017/22014; A61B 2017/00026; A61B 2017/00075; A61B 2017/00106; A61B 2017/0011
See application file for complete search history.

(56) References Cited

U.S. PATENT DOCUMENTS

| | | | | |
|---|---|---|---|---|
| 4,986,259 A * | 1/1991 | Aida | .................. | A61B 17/2256 600/439 |
| 5,042,460 A | 8/1991 | Sakurai | | |
| 5,192,889 A | 3/1993 | Myohga | | |
| 5,267,985 A | 12/1993 | Shimada et al. | | |
| 5,358,466 A * | 10/1994 | Aida | .................. | A61B 17/2256 600/439 |
| 5,540,702 A * | 7/1996 | Walz | ................ | A61B 17/22012 606/128 |
| 5,617,851 A | 4/1997 | Lipkovker | | |
| 5,720,286 A | 2/1998 | Chapelon et al. | | |
| 5,722,980 A * | 3/1998 | Schulz | ............. | A61B 17/22012 604/22 |
| 5,762,066 A | 6/1998 | Law et al. | | |
| 5,906,623 A * | 5/1999 | Peterson | .......... | A61B 17/22012 604/22 |
| 6,312,434 B1 * | 11/2001 | Sutrina | ............ | A61B 17/22012 606/127 |
| 6,402,046 B1 | 6/2002 | Loeser | | |
| 6,469,419 B2 | 10/2002 | Kato | | |
| 6,511,485 B2 * | 1/2003 | Hirt | .................. | A61B 17/22012 604/22 |
| 6,516,211 B1 | 2/2003 | Acker | | |
| 6,533,792 B2 * | 3/2003 | Menne | ............. | A61B 17/22012 606/128 |
| 6,875,220 B2 * | 4/2005 | Du | .................... | A61B 17/22012 604/22 |
| 7,108,695 B2 | 9/2006 | Witt | | |
| 7,135,029 B2 * | 11/2006 | Makin | ...................... | A61N 7/00 604/103.01 |
| 7,942,809 B2 | 5/2011 | Leban | | |
| 8,038,693 B2 | 10/2011 | Allen | | |
| 9,539,015 B2 * | 1/2017 | Ismay | ...................... | A61D 1/00 |
| 2003/0222535 A1 | 12/2003 | Gofman | | |
| 2008/0058803 A1 | 3/2008 | Kimura | | |
| 2010/0204617 A1 | 8/2010 | Ben-Ezra | | |
| 2013/0253387 A1 * | 9/2013 | Bonutti | ............. | A61H 23/0245 601/46 |
| 2014/0336665 A1 * | 11/2014 | Gavala | ............. | A61B 17/22012 606/128 |
| 2015/0088154 A1 * | 3/2015 | Vaitekunas | ............ | A61B 17/12 606/128 |

FOREIGN PATENT DOCUMENTS

| | | |
|---|---|---|
| JP | 2004534582 T | 11/2004 |
| WO | 03002189 A2 | 1/2003 |
| WO | 2012149361 A1 | 11/2012 |
| WO | 2013154708 A1 | 10/2013 |

* cited by examiner

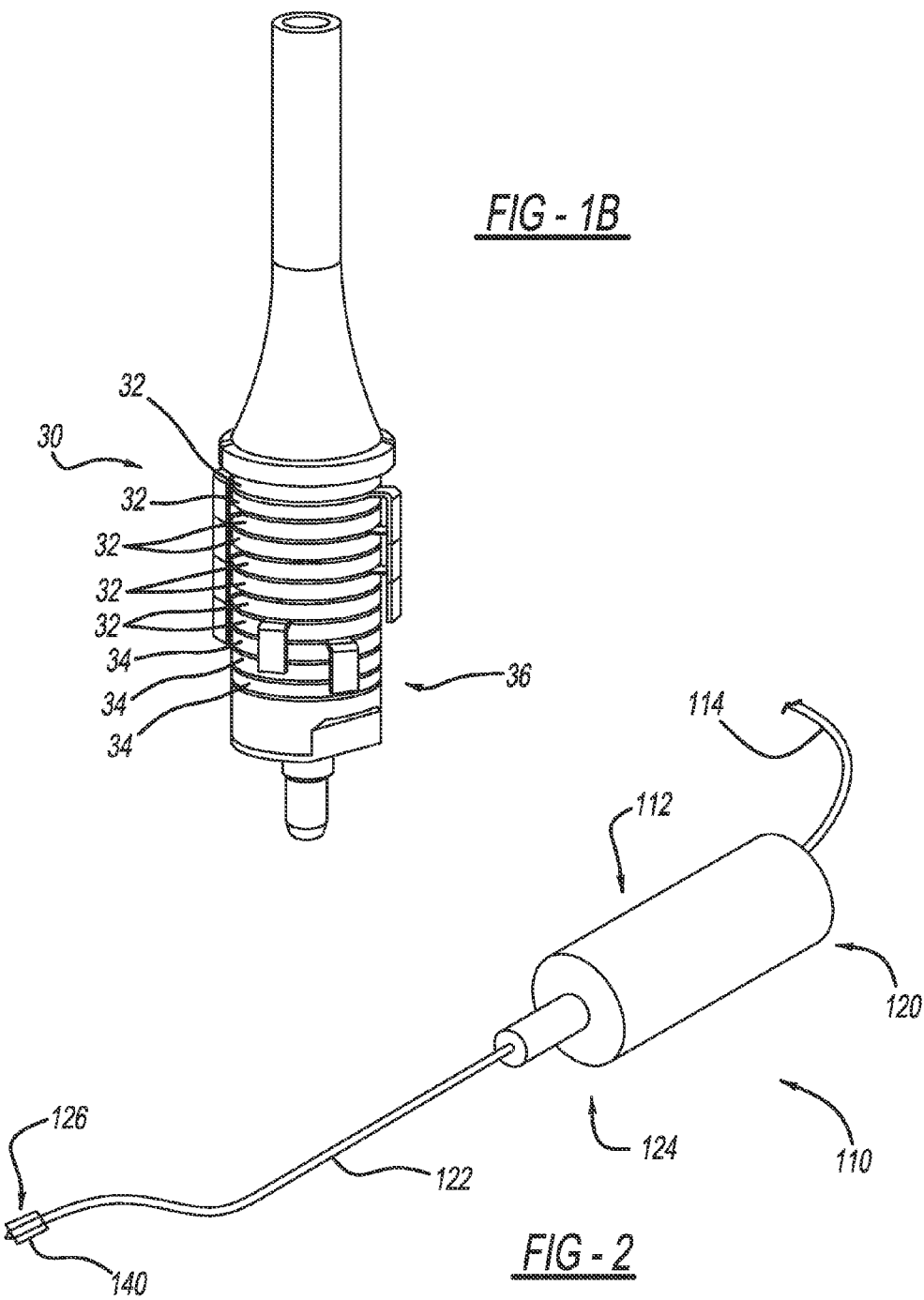

FEEDBACK DEPENDENT LITHOTRIPSY ENERGY DELIVERY

RELATED APPLICATION

This application claims the benefit of U.S. Provisional Patent Application No. 61/904,214, filed on Nov. 14, 2013, the entire contents of which are incorporated herein by reference.

FIELD

The present disclosure relates to a medical device and method, and more particularly to a lithotripter for fragmenting stones in a patient's body and a method for fragmenting stones.

BACKGROUND

The statements in this section merely provide background information related to the present disclosure and may or may not constitute prior art.

Lithotripsy is a common method for fragmenting stones, or calculi, in the urinary tract, kidneys, and/or bladder. Most lithotripsy devices use ultrasound, laser, or pneumatic energy sources to fragment such stones into smaller pieces for easier removal from the patient's urologic system. Typically, the lithotripter includes a shaft connected to an electrically controlled driver or a pneumatic actuator. The shaft is inserted into the patient's anatomy to a location near the stone, and energy of a determined pattern is sent through the shaft to impact the stone with the shaft to create a jackhammer or drilling effect on the stone. The tip of the shaft typically has a flat surface. The stone fragments are then removed by irrigation and/or baskets, typically through the center of the shaft by suction.

Among the literature that can pertain to this technology include the following patent documents and published patent applications: US 2010/0204617; U.S. Pat. No. 4,708,127; U.S. Pat. No. 5,042,460; U.S. Pat. No. 5,192,889; U.S. Pat. No. 5,358,466; U.S. Pat. No. 6,689,087; U.S. Pat. No. 8,038,693; U.S. Pat. No. 6,402,046; U.S. Pat. No. 7,942,809; US 2003/0222535; and U.S. Pat. No. 8,038,630, all incorporated by reference for all purposes.

The tip of the lithotripter shaft typically has a smooth, flat surface. Usage of tips with smooth faces on bladder, kidney, or ureter tissue has been found in studies to be safe against tissue damage or perforation. While providing more protection, however, the smooth, flat tip easily slips off of the stone, which may prolong the stone-breaking procedure as the physician repeatedly tries to contact the stone with the tip. Furthermore, if the physician applies excess pressure to the stone via the tip, the vibration of the shaft is dampened and less effective. Accordingly, there exists a need for an improved apparatus and procedure for fragmenting stones.

SUMMARY

The present disclosure provides an improved lithotripter that utilizes sensing technology and methods to determine when it is most effective to apply stone-breaking energy through a lithotripsy shaft.

Accordingly, pursuant to one aspect of the invention, which may be combined with or separate from other aspects of the invention, there is contemplated a lithotripter that comprises a lithotripsy apparatus for treatment of a urinary tract stone by fragmentation. The lithotripsy apparatus comprises a lithotripsy wave guide shaft configured to transmit an energy form to at least one urinary tract stone and a sensing device configured to provide signal data for determining optimal application of energy by the lithotripsy apparatus during treatment with the lithotripsy apparatus. A processor is configured to collect the signal data. The processor has a control logic configured to determine at least one of the following: a) if the lithotripsy wave guide shaft is in contact with a tissue; b) if the lithotripsy wave guide shaft is in contact with a stone; c) type of stone; d) if a user is applying force in excess of a predetermined threshold; and e) physical characteristics of a stone.

Accordingly, pursuant to another aspect of the invention, which may be combined with or separate from other aspects of the invention, there is contemplated a method for providing feedback to a lithotripsy apparatus having a lithotripsy shaft for fragmenting stones. The method comprises sensing an operational parameter and determining whether the operational parameter indicates at least one of the following operational conditions: a) the lithotripsy shaft is in contact with a tissue; b) the lithotripsy shaft is in contact with a stone; c) type of stone; d) amount of force being applied by a user; e) the user is applying force in excess of a predetermined threshold; and f) physical characteristics of a stone. The method further comprises providing feedback to a user regarding the at least one operational condition.

The invention may be further characterized by one or any combination of the features described herein, such as: the signal data includes at least one of current, voltage, frequency, resonance energy information, and positional information; the sensing device is at least one of a piezoelectric element, an electromagnetic element, a variable impedance element, an electro-optic element, or a strain element; the apparatus further comprises a display device configured to indicate to a user at least one of: a) whether the lithotripsy wave guide shaft is in contact with a tissue; b) whether the lithotripsy wave guide shaft is in contact with a stone; c) type of stone; d) whether a user is applying force in excess of a predetermined threshold; e) an amount of force effected upon a stone; and f) physical characteristics of a stone; the lithotripsy wave guide shaft has a distal end; the distal end has sharp edges to aggressively break up a stone; the lithotripsy wave guide shaft is straight and rigid; the lithotripsy wave guide shaft is flexible; the lithotripsy apparatus further comprises a lithotripsy driver; the lithotripsy apparatus further comprises a driver housing; the sensing device is coupled with the lithotripsy device; the method further comprises displaying to a user at least one of the following: a) whether the lithotripsy shaft is in contact with a tissue; b) whether the lithotripsy shaft is in contact with a stone; c) type of stone; d) an amount of force effected upon a stone by the user; e) whether the amount of force effected upon a stone by the user is above or below a predetermined threshold; and f) physical characteristics of a stone; the method further comprises determining whether to deliver stone-breaking energy through the lithotripsy shaft, based on the operational condition; the method further comprising determining an amount of stone-breaking energy to deliver through the lithotripsy shaft, based on the operational condition; the method further comprising delivering stone-breaking energy through the lithotripsy shaft; and the step of sensing an operational parameter includes delivering a sensing energy through the lithotripsy shaft, the sensing energy being lesser than the stone-breaking energy.

Further aspects, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1B is a perspective view of a piezoelectric stack of the lithotripter of FIG. 1A, according to the principles of the present disclosure;

FIG. 2 is a schematic perspective view of another lithotripter for fragmenting stones, in accordance with the principles of the present disclosure;

DETAILED DESCRIPTION

The following description is merely exemplary in nature and is not intended to limit the present disclosure, application, or uses. The present invention relates to a lithotripter for fragmenting stones.

A lithotripter for fragmenting a stone inside a patient's body is provided. The lithotripter may include a lithotripsy apparatus for treatment of a urinary tract stone by fragmentation. The lithotripsy apparatus, for example, comprises a lithotripsy wave guide shaft configured to transmit an energy form to at least one urinary tract stone and a sensing device configured to provide signal data for determining optimal application of energy by the lithotripsy apparatus during treatment with the lithotripsy apparatus. A processor is configured to collect the signal data. The processor has a control logic configured to determine at least one of the following: a) if the lithotripsy wave guide shaft is in contact with a tissue; b) if the lithotripsy wave guide shaft is in contact with a stone; c) type of stone; d) if a user is applying force in excess of a predetermined threshold; and e) physical characteristics of a stone.

Figure 1A:
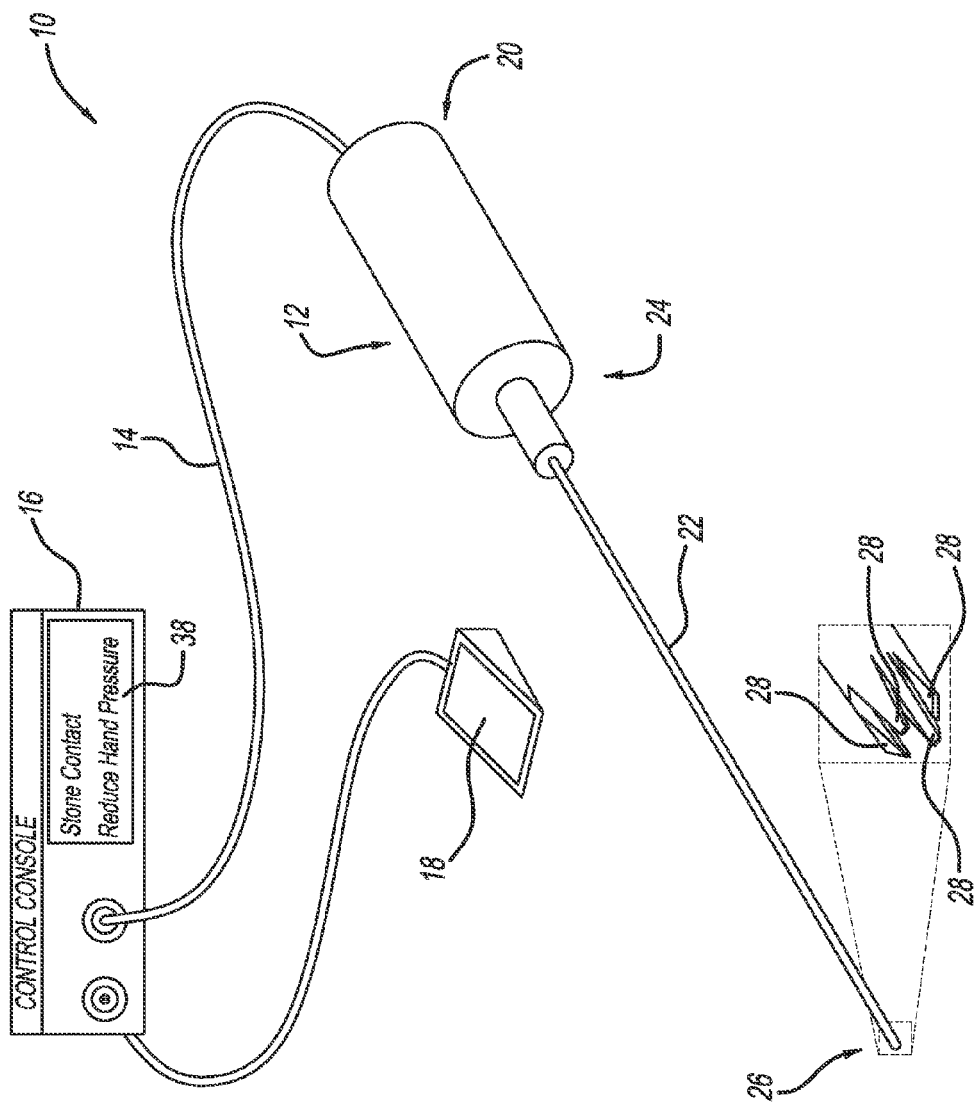
FIG. 1A is a schematic perspective view of a lithotripter for fragmenting stones, in accordance with the principles of the present disclosure.

With reference to the figures, wherein like numerals indicate like components, and specifically with reference to FIG. 1A, an example of a lithotripter in accordance with the principles of the present disclosure is illustrated and generally designated at 10. The lithotripter 10 may be used for fragmenting stones in a patient's anatomy, such as in a patient's urinary tract, bladder, or kidneys.

The lithotripter 10 includes a handle 12 that houses a piezoelectric driver 30 (shown in FIG. 1B). The driver 30 is connected by a cable 14 to a control console 16, which may be driven by a foot pedal 18, by way of example. In this example, the cable 14 is connected to the driver 30 through a proximal end 20 of the handle 12. A wave guide shaft 22 is connected to a distal end 24 of the handle 12.

The wave guide shaft 22 may be rigid, semi-rigid, or flexible, by way of example. In the example of FIG. 1A, the wave guide shaft 22 is illustrated as being rigid. The wave guide shaft 22 is provided for transmitting a waveform generated by the driver 30 to at least one stone, such as a urinary tract stone. Thus, the wave guide shaft 22 is configured to transmit an energy form to the urinary tract stone. The wave guide shaft 22 may be partially inserted into the patient through the patient's urethra or percutaneously by way of an incision through the patient's skin, by way of example. The waveforms may be delivered to the stone by way of the distal end 26 of the wave guide shaft 22. The distal end 26 may be pressed up against a stone to create a jackhammer effect on the stone and break up the stone, by way of example. In the illustrated example, the distal end 26 of the wave guide shaft 22 has a plurality of sharp prongs 28 extending therefrom. The sharp prongs 28 may have sharp edges to aggressively break up a stone. The sharp prongs 28 may be tapered, beveled, or a combination of both tapered and beveled, by way of example. The prongs 28 help secure the wave guide shaft 22 to a stone when the lithotripter 10 is being operated. It should be understood, however, that the end 26 could have any shape, such as a smooth, flat surface or a different shape textured surface.

Referring now to FIG. 1B, the driver 30 is illustrated, which is in the form of a piezoelectric stack in this variation. It should be understood that, in this example, the piezoelectric driver 30 is not shown in FIG. 1A because the piezoelectric driver 30 is housed in the handle 12 of the lithotripter 10. The piezoelectric driver 30 is configured to drive the lithotripter 10 when an electric charge is applied to a stack of first elements 32, which ultimately sends a longitudinal vibration through the wave guide shaft 22 to create a jackhammer effect on a stone when the wave guide shaft 22 is in contact with the stone.

A piezoelectric sensor 36 is disposed adjacent to the piezoelectric driver 30. Both the piezoelectric sensor 36 and the piezoelectric driver 30 are disposed in the handle 12 in this example, and thus, the piezoelectric sensor 36 and the piezoelectric driver 30 are coupled together. The piezoelectric sensor 36 includes a stack of second elements 34 disposed adjacent to the stack of first elements 32. The piezoelectric sensor 36 is not configured to be energized by an electric energy source like the piezoelectric driver 30. Rather, the stack of second elements 34 acts as a sensor. For example, when subject to vibration, the second elements 34 will vibrate. The mechanical strain on the second elements 34 created by the vibration may then be measured and converted to an electrical signal.

Thus, the piezoelectric sensor 36 is part of a sensing device that is configured to provide signal data based on the mechanical strain and/or vibration of the piezoelectric sensor 36. The strain and/or vibration of the piezoelectric sensor 36 may be related to the state of the end 26 or other parts of the shaft 22. In other words, a different state is sensed based on whether the shaft 22 is in contact with a stone or not in contact with a stone; or more specifically, a different vibration or strain is measured based on whether the shaft is in contact with a stone. Similarly, if the shaft 22 is pressed against a stone with excessive force, the sensor 36 may be able to sense the same based on the amount of vibration and/or strain to which the second elements 34 have been subjected. Accordingly, the piezoelectric sensor 36 may be used to determine optimal application of energy by the lithotripsy apparatus 10 during treatment with the lithotripsy apparatus 10.

Though the piezoelectric sensor 36 is illustrated as being discrete from and disposed adjacent to the piezoelectric driver 30 in FIG. 1B, it should be understood that, in some variations, the piezoelectric sensor 36 and the piezoelectric driver 30 may be a unitary device, wherein the elements of the stack may be used as both the driver and the sensor. In one variation, an extra element 32 of the piezoelectric driver 30 is used as the piezoelectric sensor. Information from the sensor 36 may be either dependent or independent from the stimulating energy.

The control console 16 includes a processor configured to collect the signal data regarding an operational parameter, such as current, voltage, or frequency, which could be based on vibration or strain, or other measurable parameters, to determine an operational condition. In some variations, the processor includes a control logic configured to determine at least one of the following operational conditions, based on the measured operational parameter: a) if the wave guide shaft 22 is in contact with a tissue, such as a cavity wall of the patient; b) if the wave guide shaft 22 is in contact with a stone; c) type of stone; d) if a user is applying force in excess of a predetermined threshold; and e) physical characteristics of a stone. The detection of stone contact may indicate that it would be suitable to apply stone-breaking energy to the shaft 22, and the detection of no stone contact may indicate that it would not be suitable to apply stone-breaking energy to the shaft 22. Applied force information might be used to adjust the drive frequency, amplitude or other characteristic. Such an adjustment may be made to improve the performance of the lithotripter given the level of applied force, or it may be made to cease supplying the drive energy to reduce or prevent tissue damage.

Analysis might be used to determine what kind of stone, or stone hardness, or stone size was encountered, and the lithotripsy energy delivered may then be tailored to provide a better stone-breaking effect based on the stone characteristics detected. For example, the frequency, drive pattern, or modulation might be adjusted based on the information detected. Detection of resonance energy reduction may be used to identify the effect of too much force being applied by the user, thus diminishing the effectiveness of the applied stone-breaking energy. If the force detected exceeds a predetermined threshold, an alert may be provided to the user to reduce the applied force. The predetermined threshold could be any suitable amount, such as, for example, 1500 g.

To break up a stone, a high frequency of about 21.4 kHz, square wave 50% duty cycle could be used, with a gating/modulating low frequency of different ranges. For coarse fragmentation and large stones of about 10-20 mm, the low frequency used for gating the ultrasonic frequency could be a sweeping 5-30 Hz. Optionally, for medium size stones of about 5-10 mm, the low frequency range used for gating the ultrasonic frequency could be a sweeping 25-50 Hz. For fine fragmentation and small size stones of about 1-7 mm, the low frequency range used for gating the ultrasonic frequency could be a sweeping 60-90 Hz. The displacement at the end 26 could be about 20 μm for the ultrasonic frequency and about 0.5-2 mm for the mechanical oscillation in an unloaded state (e.g., in free air).

The signal data that is provided by the piezoelectric sensor 36 to the processor could include one or more of the following operational parameters: current, voltage, frequency, and resonance energy information. The control console 16 includes a display window 38 configured to indicate to a user one or more of the following operational conditions: a) whether the wave guide shaft 22 is in contact with a tissue, such as a cavity wall; b) whether the wave guide shaft 22 is in contact with a stone; c) type of stone; d) whether a user is applying force in excess of a predetermined threshold; e) an amount of force effected upon a stone; and f) physical characteristics of a stone.

In FIG. 1A, the wave guide shaft 22 is straight and rigid. It should be understood, however, that the wave guide shaft 22 could alternatively be semi-rigid or flexible.

The lithotripter 10 may have portions (not shown) forming a lumen or channel through the wave guide shaft 22 for suctioning and/or irrigating a urinary tract. For example, the wave guide shaft 22 may have a lumen formed through the center of the wave guide shaft 22 and extending along the length of the wave guide shaft 22. In addition, the handle 12 may have openings formed through both the proximal and distal ends 20, 24 of the handle 12.

The driver 30 may take on various forms, without departing from the spirit and scope of the present invention. For example, the driver 30 could have ultrasonic and/or sonic driver components, and it need not be solely a piezoelectric driver. Instead, the driver 30 could also comprise electromagnetic coils, such as a voice coil motor, in one variation. In some forms, the driver 30 could be configured to produce a waveform at a frequency that oscillates at a natural frequency, or resonance frequency, of the targeted stone.

Referring now to FIG. 2, another example of a lithotripter is illustrated and generally designated at 110. Like the lithotripter 10 hereinbefore described in FIG. 1A, the lithotripter 110 shown in FIG. 2 may be used for fragmenting stones in a patient's anatomy, such as in a patient's urinary tract, bladder, or kidneys. Similar to the lithotripter 10 shown above, the lithotripter 110 may include a handle 112 that houses a piezoelectric driver (not shown, see FIG. 1B for a similar piezoelectric driver 30). The driver and handle 112 are connected by a cable 114 to a control console (not shown, see FIG. 1A for a similar control console 16). In this example, the cable 114 is connected to a proximal end 120 of the handle 112. A wave guide shaft 122 is connected to a distal end 124 of the handle 112.

The wave guide shaft 122 is illustrated as being flexible, in this example, however, it should be understood that the wave guide shaft 122 could alternatively be semi-rigid or rigid. The wave guide shaft 122 is provided for transmitting a wave form generated by the driver to at least one stone, such as a urinary tract stone. Thus, the wave guide shaft 122 is configured to transmit an energy form to the urinary tract stone. For the case of a flexible wave guide shaft, the energy form transmitted through the shaft to deliver stone breaking energy to a urinary tract stone may preferably be transverse or shear waves. For example, the wave guide shaft 122 may be partially inserted into the patient through the patient's urethra or percutaneously by way of an incision through the patient's skin, by way of example. The waveforms may be delivered to the stone by way of the end 126 of the wave guide shaft 122. The end 126 may be pressed up against a stone to deliver the transverse or shear waves to the stone and break up the stone, by way of example. The end 126 of the wave guide shaft 122 may include a plurality of sharp prongs, as illustrated at reference numeral 28 in FIG. 1A, a flat surface, or any other desired shape.

A sensing device 140 is attached to, or coupled to, the end 126 of the wave guide shaft 122. The sensing device 140 may be incorporated into, coaxial with, attached to, or coupled in any suitable way to the end 126 of the wave guide shaft 122. The sensing device 140 could alternatively be attached to another portion of the lithotripter 110, other than the end 126 of the wave guide shaft 122. For example, the sensing device 140 could be disposed in the handle 112. The sensing device 140 could include one or more piezoelectric elements, one or more electromagnetic elements, one or more electro-optic elements, one or more strain elements or strain gauges, a vibration sensor, laser, a Doppler device, a variable impedance element, an electro-optical impedance element, a flow rate sensor, an accelerometer, a shaft displacement sensor, or any other suitable sensing device.

The sensing device 140 is configured to provide signal data to the processor, which may be included in the control console 16, as described above. The sensing device 140 is configured to sense different operational parameters, based on whether the shaft 122 is in contact with a stone or not in contact with a stone. Similarly, the sensing device is configured to sense an operational parameter that may indicate whether the shaft 122 is pressed against a stone with excessive force. Accordingly, the sensing device 140 may be used to determine optimal application of energy by the lithotripsy apparatus 110 during treatment with the lithotripsy apparatus 110, as described above with respect to the lithotripter 10 of FIG. 1A. There may be more than one sensing device and may be more than one type of sensing device. The sensing device detecting excessive force may trigger a warning signal to the user and/or a cessation of stone breaking energy in order to protect the patient and/or guide to user in applying more optimum stone breaking force.

The sensing device 140 may be used to measure movement of the handle 112 to determine the angle and speed of stone penetration. Movement of the shaft 122 inside the handle 112 could be measured, for example. Rate and direction of motion could be measured to determine the forward (axial) speed of movement of the handle 112 or shaft 122, for example. The orientation of the lithotripter 110 relative to a force sensor can help to determine off-axis forces on the shaft. The sensing device 140 may be used to determine how far into a stone the device 140 is penetrating by observing the force and forward speed of movement of the lithotripsy shaft 122. Feedback from the sensing device 140 to the user via the control console (similar to control console 16, but not shown in FIG. 2) would allow for use of optimal operational parameters through refinement of applied energy characteristics to facilitate faster and more complete stone destruction.

The sensing device 140 may be used to measure a flow rate of air or fluid during use of a suction function. During the case where the suction function is blocked or impeded, an indicator may be sent to control console to indicate to a user that there is a shaft blockage. This indication may trigger to a user to perform a shaft blockage clearing sequence. A shaft blockage clearing sequence may include reversing suction and forcing the shaft blockage free with forced air or fluid, for example. An alternative shaft blockage clearing sequence may include indicating to a user to remove lithotripsy apparatus 110 from the patient, pulsing forced air or fluid, applying an aggressive vibrational waveform to rattle the shaft blockage loose, or utilization of a shaft clearing tool, for example.

Figure 3:
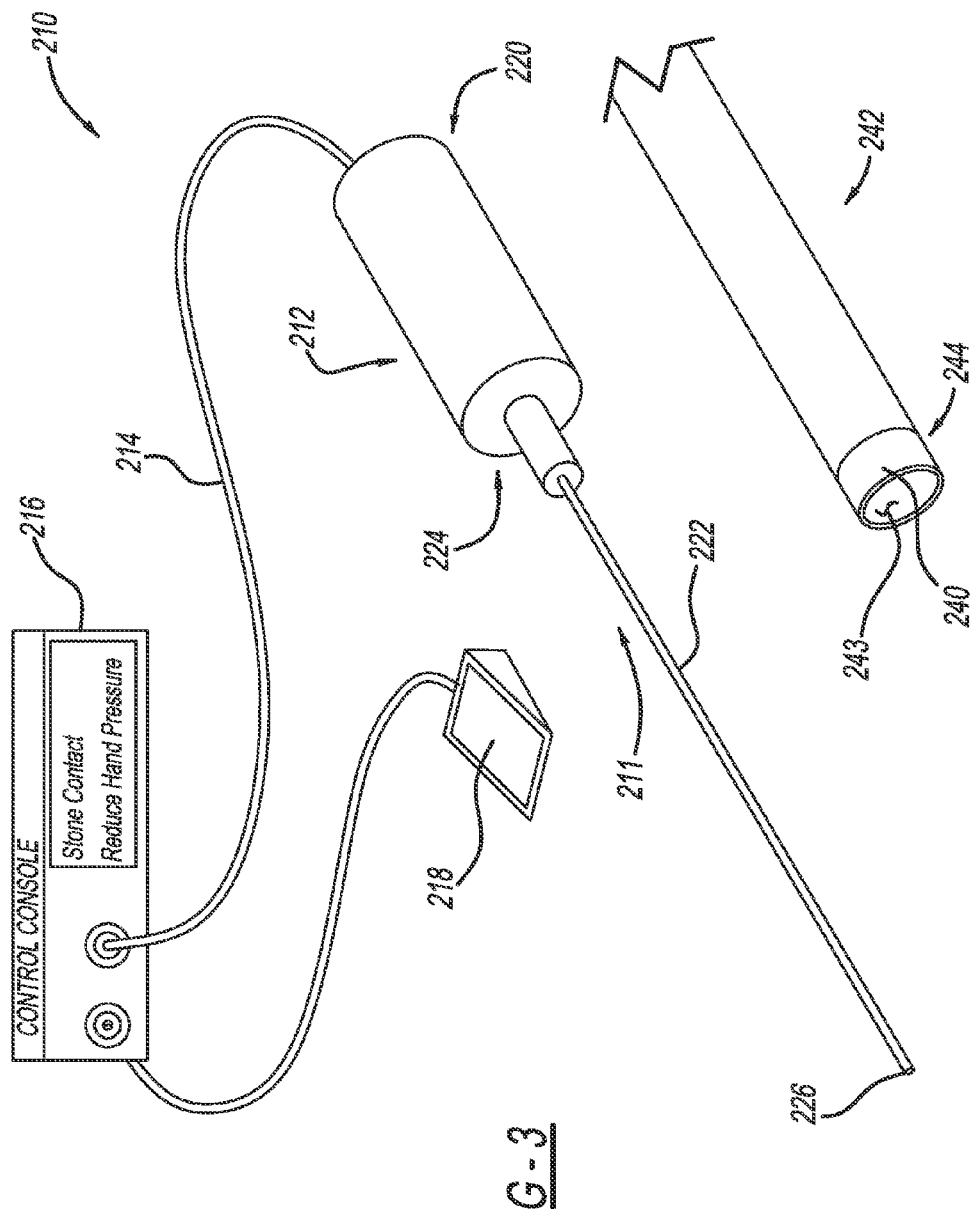
FIG. 3 is a schematic perspective view of yet another lithotripter for fragmenting stones, in accordance with the principles of the present disclosure.

Referring now to FIG. 3, yet another example of a lithotripter is illustrated and generally designated at 210. Like the lithotripter 10 hereinbefore described in FIG. 1A, the lithotripter 210 shown in FIG. 3 may be used for fragmenting stones in a patient's anatomy, such as in a patient's urinary tract, bladder, or kidneys. The lithotripter 210 includes a lithotripsy apparatus 211 that includes a handle 212 and a wave guide shaft 222 extending from the handle 212. The handle 212 houses a piezoelectric driver (not shown, see FIG. 1B for a similar piezoelectric driver 30). The driver and handle 212 are connected by a cable 214 to a control console 216, which may be driven by a foot pedal 218. In this example, the cable 214 is connected to a proximal end 220 of the handle 212. The wave guide shaft 222 is connected to a distal end 224 of the handle 212.

The wave guide shaft 222 is illustrated as being straight and rigid, in this example; however, it should be understood that the wave guide shaft 222 could alternatively be semi-rigid or flexible. The wave guide shaft 222 is provided for transmitting a waveform generated by the driver to at least one stone, such as a urinary tract stone. Thus, the wave guide shaft 222 is configured to transmit an energy form to the urinary tract stone. The wave guide shaft 222 may be partially inserted into the patient through the patient's urethra or percutaneously by way of an incision through the patient's skin, by way of example. The waveforms may be delivered to the stone by way of the end 226 of the wave guide shaft 222. The distal end 226 may be pressed up against a stone to create a jackhammer effect on the stone and break up the stone, by way of example. The distal end 226 of the wave guide shaft 222 may include a plurality of sharp prongs, as illustrated as reference numeral 28 in FIG. 1A, a flat surface, or any other desired shape. It is contemplated that through the feedback dependent surgical device of the present invention that feedback indicating whether a tip is in contact with bone, cartilage, or tissue, for example, may provide information which can be used to adjust waveform frequency and amplitudes.

The lithotripter 210 may include an independent sheath, such as an access sheath 242, that is used in conjunction with the lithotripsy apparatus 211. For example, a physician could place the lithotripsy apparatus 211 inside an access sheath 242 when performing a stone-breaking procedure. Access sheath 242 could be an endoscope, percutaneous nephrolithotomy (PCNL) access sheath, a ureteral access sheath or the like. The access sheath may be provided with a sensing capability. The access sheath may be electrically connected to the lithotripsy apparatus to facilitate communication back to the user via control console 216. The lithotripsy apparatus 211 could be inserted through a working channel 243 defined by the cylindrical wall of the access sheath 242 to gain access to the stone. The access sheath 242 includes a sensing device 240 disposed circumferentially on a distal end 244 of the access sheath 242. However, it should be understood that the sensing device 240 could alternatively be disposed in another location of the access sheath 242, such as in a handle (not shown) of the access sheath 242. The sensing device 240 may be incorporated into, coaxial with, or attached in any suitable way to the end 244 or another part of the access sheath 242 or another device. The sensing device 240 could include one or more piezoelectric elements, one or more electromagnetic elements, one or more electro-optic elements, one or more strain elements or strain gauges, a vibration sensor, laser, a Doppler device, or any other suitable sensing device.

In another variation (not shown), rather than provide the sheath as an access sheath 242, the sheath bearing the sensing device 240 may be an endoscope, and the sensing device 240 could be a camera with a light, disposed on the distal end of the endoscope.

The sensing device 240 may be configured to provide signal data to the processor, which may be included in the control console 216, as described above. The sensing device 240 may be configured to sense different values of operational parameters including speed of vibration of shaft 222 as well as displacement of shaft 222, for example, to help determine if shaft 222 is in contact with a stone or not in contact with a stone. Similarly, the sensing device 240 may be configured to sense whether a suction flow rate is slowed or stopped due to blockage from a large stone. Accordingly, the sensing device 240 may be used to determine optimal application of energy by the lithotripsy apparatus 211 during treatment with the lithotripsy apparatus 211, as described above with respect to the lithotripters 10, 110 of FIGS. 1A and 2.

Figure 4:
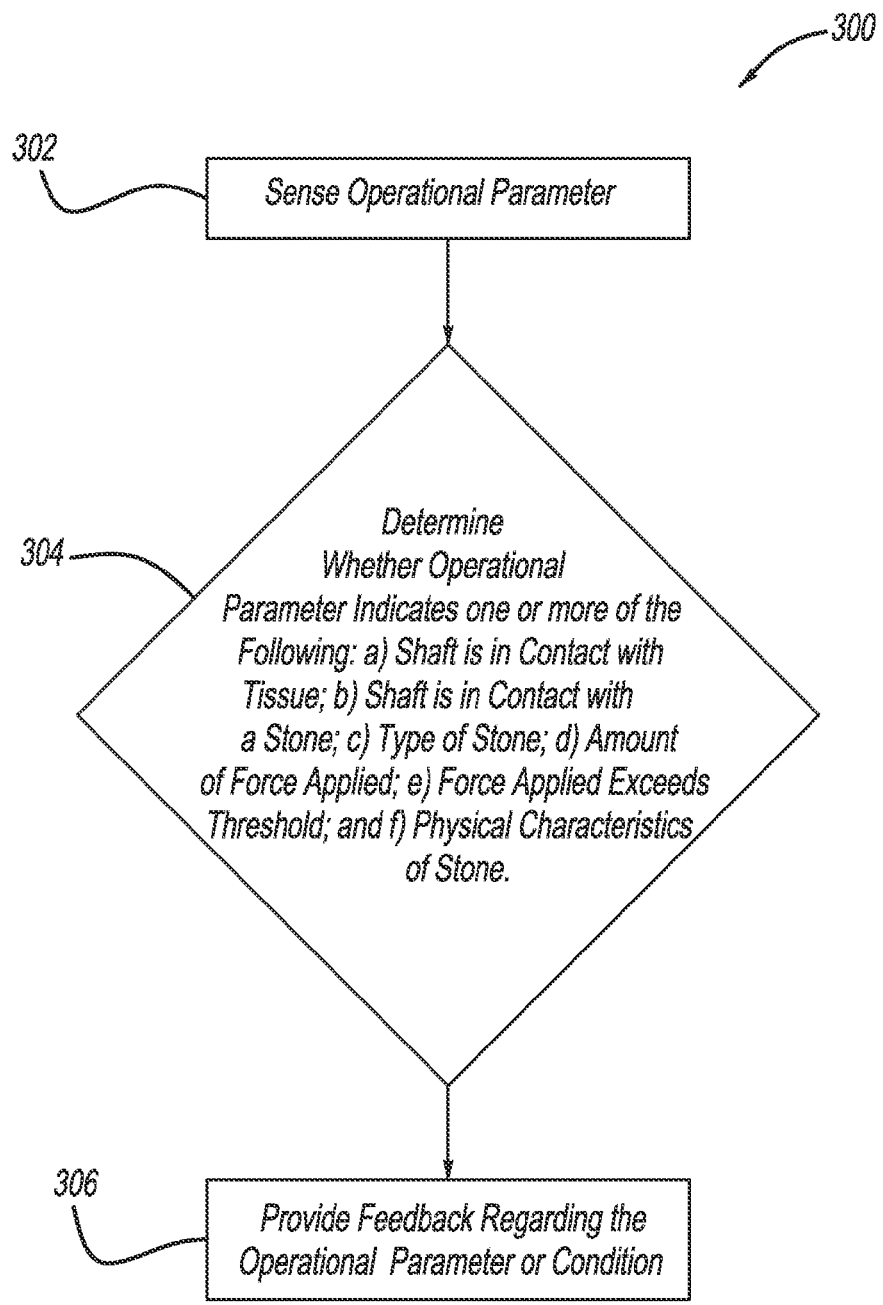
FIG. 4 is a block diagram illustrating a method for fragmenting stones, according to the principles of the present disclosure.

Referring now to FIG. 4, a method for providing feedback to a lithotripsy apparatus having a lithotripsy shaft for fragmenting stones is illustrated in a block diagram and generally designated at 300. The method 300 includes a step 302 of sensing an operational parameter of the lithotripter system. For example, the step 302 could include sensing a parameter such as strain, vibration, or any other suitable parameter.

The method 300 further includes a step 304 of determining whether the operational parameter indicates at least one of the following operational conditions: a) the lithotripsy shaft is in contact with a tissue; b) the lithotripsy shaft is in contact with a stone; c) type of stone; d) amount of force being applied by a user; e) the user is applying force in excess of a predetermined threshold; and/or f) physical characteristics of a stone.

The method 300 includes a step 306 of providing feedback to a user regarding the operational parameter or condition that has been sensed or determined. The feedback may be provided by way of the display 38 on the control console 16, 216, through an audio signal, or in any other suitable manner. For example, the step 306 of the method 300 could include displaying to a user at least one of: a) whether the lithotripsy shaft is in contact with a tissue; b) whether the lithotripsy shaft is in contact with a stone; c) type of stone; d) amount of force effected upon a stone by the user; e) whether the amount of force effected upon a stone by the user is above or below a predetermined threshold; and f) physical characteristics of a stone. The user can then determine whether to deliver stone-breaking energy through the lithotripsy shaft, based on the operational condition, and the user can also determine the amount of stone breaking energy to deliver through the lithotripsy shaft, based on the at least one operational condition. The method could further include delivering stone-breaking energy through the lithotripsy shaft when it is determined that such an energy should be applied.

The step 302 of sensing an operational parameter may include delivering a sensing energy through the lithotripsy shaft, wherein the sensing energy is lesser than the stone-breaking energy. For example, the piezoelectric driver 30 may be used to generate a sensing energy for the purposes of measuring the vibration, strain, or other parameter and determining whether the shaft is in contact with a stone or tissue, characteristics of the stone, or the amount of force that is being applied. Thereafter, once it is determined that a stone-breaking energy should be applied, the user can then increase the amount of energy from the sensing level of energy to the stone-breaking level of energy. The sensing energy level is much lower than the stone-breaking energy level, such that the sensing energy is merely used to obtain a measurement of the operational parameter and does little to alter or break up stones or other tissue. The stone-breaking energy is a high level of energy that is sufficient to break up a stone.

Figure 5A:
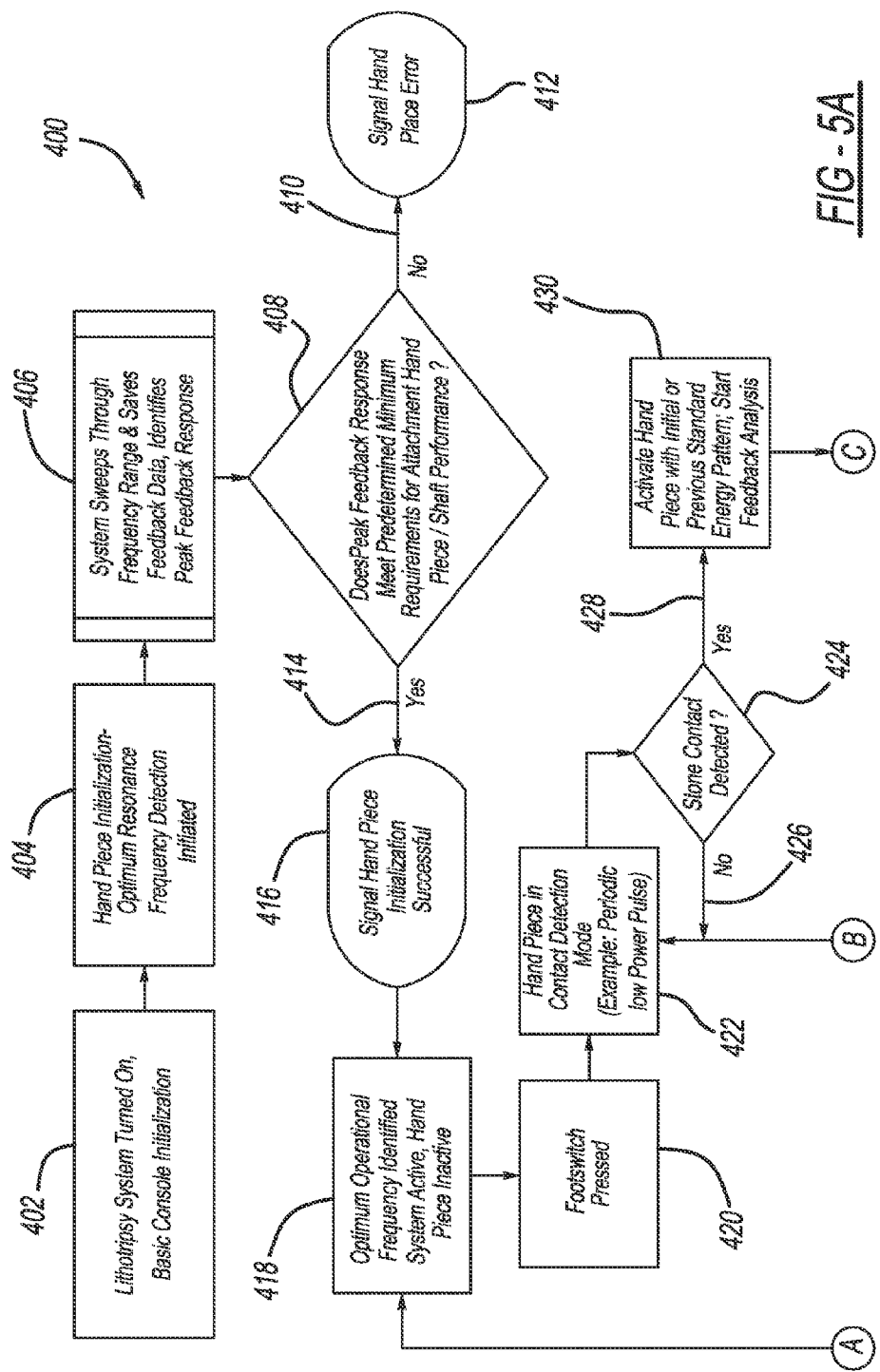
FIG. 5A is a block diagram illustrating a first portion of another method for fragmenting stones, which may be used in conjunction with the method of FIG. 4, in accordance with the principles of the present disclosure.
Figure 5B:
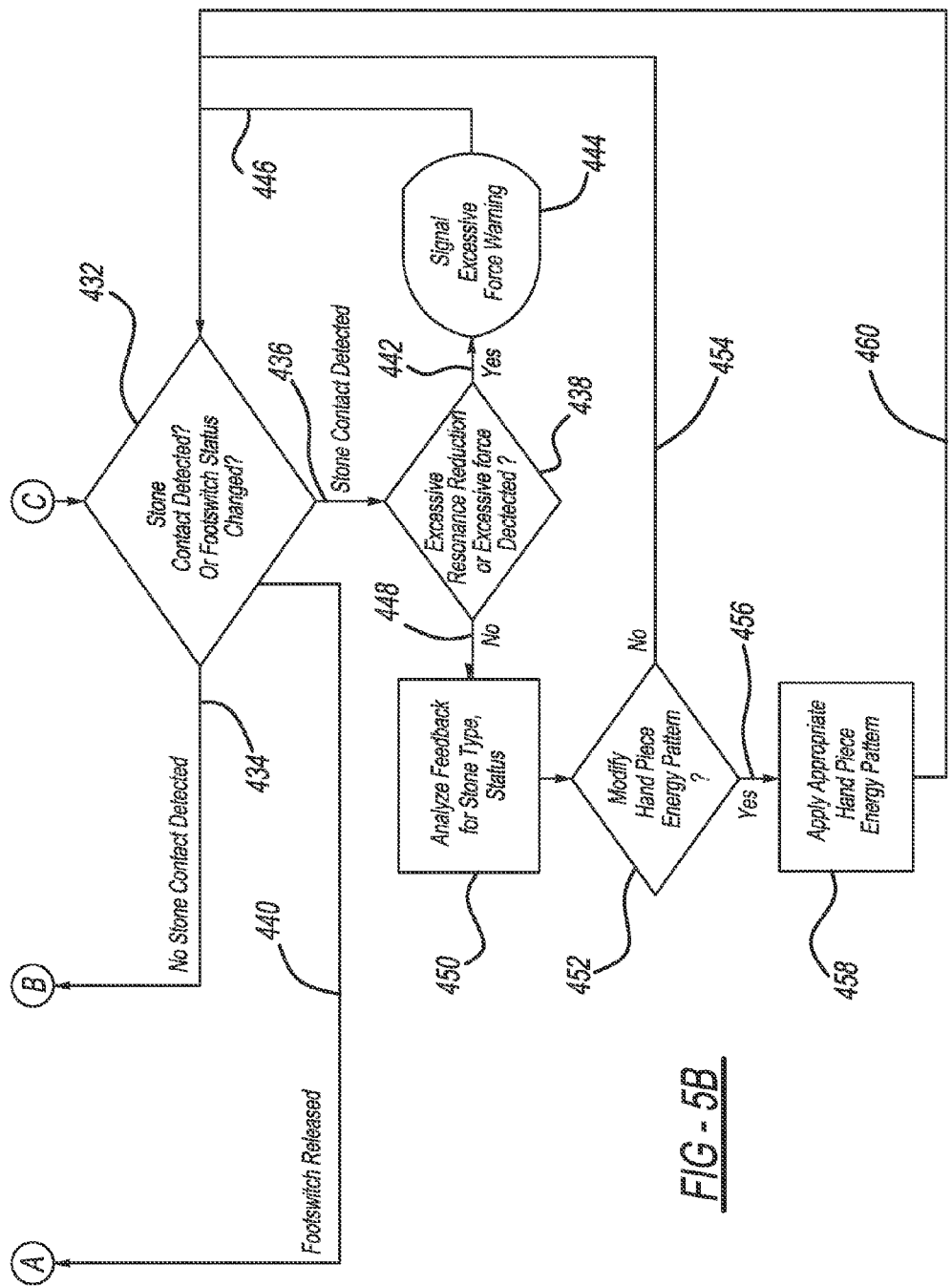
FIG. 5B is a block diagram illustrating a second portion the method of FIG. 5A, according to the principles of the present disclosure.

Referring now to FIGS. 5A-5B, a more detailed version of a method for providing feedback to a lithotripsy apparatus having a lithotripsy shaft for fragmenting stones is illustrated in a block diagram and generally designated at 400. The method 400 begins with a step 402 of turning on the lithotripsy system and performing basic console initialization. The method 400 then includes a step 404 of initializing the hand piece and initiating optimum resonance frequency detection. The method 400 includes a step 406 of sweeping through the system's frequency range, saving feedback data, and identifying the peak feedback response.

Once steps 402-406 are complete, the method 400 proceeds to a step 408 of determining whether the peak feedback response meets a predetermined minimum requirement for the attached hand piece and shaft performance. If no, the method 400 follows a path 410 to a step 412 that indicates that a handpiece error signal is issued to the console and/or the user. If yes, the method 400 follows a path 414 to a step 416 that indicates that the signal handpiece initialization was successful. The method 400 then proceeds to a step 418. In some variations, the step 416 could be eliminated, and the method 400 could proceed to step 418 without completing step 416.

In step 418, the optimum operational frequency is identified, the system is identified as active, and the hand piece is inactive. In step 420, the footswitch is pressed. The method 400 then proceeds to step 422, in which the hand piece is put into contact detection mode. For example, in this step 422, a periodic low power pulse could be applied. The method 400 next proceeds to step 424, in which it is determined whether a stone contact is detected. If no, the method 400 proceeds along a path 426 back to the step 422, in which the hand piece is in detection mode. If yes, however, the method 400 proceeds along a path 428 to a step 430 that includes activating the hand piece with an initial (or previous) standard energy pattern and starting the feedback analysis. The standard energy pattern is the low-level sensing energy described above, wherein applying the standard energy level allows the position and other operational conditions to be sensed, combined with a high level stone breaking energy pattern, or only a high level stone breaking energy pattern is applied but is monitored for continued stone contact detection.

Next, the method 400 proceeds to a step 432 in which it is determined whether a stone is detected or whether the footswitch status has changed. If no stone is detected, the method 400 proceeds along a path 434 back to step 422. If a stone is detected, however, the method 400 proceeds along a path 436 to a step 438. If the footswitch is released, the method 400 proceeds along a path 440 back to step 418 (or 420).

In step 438, the method 400 includes determining whether excessive resonance reduction has occurred or whether excessive force has been detected. If yes, the method 400 proceeds along path 442 to a step 444, where a signal excessive force warning is activated. From step 444, the method 400 proceeds along path 446 back to step 432. If, however, there is no excessive resonance reduction or excessive force, the method 400 proceeds along path 448 to step 450.

In step 450, the method 400 includes analyzing the feedback for stone type and status (e.g., whether there is contact with a stone). The method 400 then proceeds to step 452 in which the method 400 determines whether to modify the energy pattern. If no, the method 400 proceeds along path 454 back to step 432. If yes, the method 400 proceeds along path 456 to step 458.

In step 458, the method 400 includes applying an appropriate hand piece energy pattern. From step 458, the method 400 proceeds along a path 460 back to step 432, thereby providing a continuous monitoring process for stone contact and energy control (footswitch) status while stone breaking energy is applied.

It should be understood that the methods 300, 400 described in FIGS. 4, 5A, and 5B are merely examples, and variations may occur without departing from the spirit and scope of the invention, as defined by the claims. Likewise, the specific illustrations of the lithotripters 10, 110, 210 are examples and are not meant to limit the invention in any way. The description of the invention is merely exemplary in nature and variations that do not depart from the gist of the invention are intended to be within the scope of the invention. Such variations are not to be regarded as a departure from the spirit and scope of the invention. For example, variations in the various figures can be combined with each without departing from the spirit and scope of the present disclosure.

The preferred embodiment of the present invention has been disclosed. A person of ordinary skill in the art would realize, however, that certain modifications would come within the teachings of this invention. Therefore, the following claims should be studied to determine the true scope and content of the invention.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints, the use of "about" or "approximately" in connection with a range apply to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

What is claimed is:

1. A lithotripter, comprising:
    a lithotripsy apparatus for treatment of a urinary tract stone by fragmentation, the lithotripsy apparatus comprising a lithotripsy wave guide shaft configured to transmit an energy at two different frequencies to at least one urinary tract stone;
    a sensing device configured to provide signal data for determining optimal application of the energy by the lithotripsy apparatus during treatment with the lithotripsy apparatus; and
    a processor configured to collect the signal data, the processor having a control logic configured to optimize the two frequencies after determining:
        a) if the lithotripsy wave guide shaft is in contact with a stone;
        b) type of stone;
        c) if a user is applying force in excess of a predetermined threshold; and
        d) physical characteristics of a stone
    from the signal data.

2. The apparatus of claim 1, wherein the signal data includes at least one of current, voltage, frequency, resonance energy information, and positional information.

3. The apparatus of claim 1, wherein the sensing device is at least one of a piezoelectric element, an electromagnetic element, an electro-optic element, an electro-impedance element, a variable impedance element, a strain element, a flow rate sensor, an accelerometer, and a displacement sensor.

4. The apparatus of claim 1, further comprising a display device configured to indicate to a user at least one of:
    a) whether the lithotripsy wave guide shaft is in contact with a tissue;
    b) whether the lithotripsy wave guide shaft is in contact with a stone;
    c) type of stone;
    d) whether a user is applying force in excess of a predetermined threshold;
    e) an amount of force effected upon a stone; and
    f) physical characteristics of a stone.

5. The apparatus of claim 1, the lithotripsy wave guide shaft having a distal end, the distal end having sharp edges to aggressively break up a stone.

6. The apparatus of claim 1, wherein the lithotripsy wave guide shaft is straight and rigid.

7. The apparatus of claim 1, wherein the lithotripsy wave guide shaft is flexible.

8. The apparatus of claim 1, the lithotripsy apparatus further comprising a lithotripsy driver and a driver housing.

9. The apparatus of claim 1, wherein the sensing device is coupled with at least one of the lithotripsy device and a sheath at least partially surrounding the lithotripsy device.

10. The apparatus of claim 1, wherein the waveguide shaft transmits the energy at two frequencies simultaneously.

11. A method for optimizing a lithotripsy apparatus having a lithotripsy shaft configured to transmit an energy at two different frequencies for fragmenting stones, the method comprising:
    sensing with a sensing device an operational parameter for adjusting the stone-fragmenting energy;
    wherein a processor determines the operational parameter after collecting signal data indicating the following operational conditions:
        a) the lithotripsy shaft is in contact with a stone;
        b) type of stone;
        c) amount of force being applied by a user;
        d) whether the user is applying force in excess of a predetermined threshold; and
        e) physical characteristics of a stone;
    and optimizing two frequencies according to the operational conditions.

12. The method of claim 11, further comprising displaying to a user at least one of:

a) whether the lithotripsy shaft is in contact with a tissue;
b) whether the lithotripsy shaft is in contact with a stone;
c) type of stone;
d) an amount of force effected upon a stone by the user;
e) whether the amount of force effected upon a stone by the user is above or below a predetermined threshold; and
f) physical characteristics of a stone.

13. The method of claim 12, further comprising determining whether to deliver stone-breaking energy through the lithotripsy shaft, based on the operational conditions.

14. The method of claim 13, further comprising determining an amount of stone-breaking energy to deliver through the lithotripsy shaft, based on the operational conditions.

15. The method of claim 11, wherein the optimization is an adjustment to a waveform frequency and amplitude.

16. The method of claim 15, wherein the step of sensing an operational parameter includes delivering a sensing energy through the lithotripsy shaft, the sensing energy being lesser than the stone-fragmenting energy.

* * * * *